US007143031B1

(12) United States Patent
Ahroon

(10) Patent No.: US 7,143,031 B1
(45) Date of Patent: Nov. 28, 2006

(54) DETERMINING SPEECH INTELLIGIBILITY

(75) Inventor: William A. Ahroon, Enterprise, AL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 841 days.

(21) Appl. No.: 10/025,042

(22) Filed: Dec. 18, 2001

(51) Int. Cl.
*G10L 11/00* (2006.01)

(52) U.S. Cl. ....................................... 704/224

(58) Field of Classification Search .................. None
See application file for complete search history.

(56) References Cited

U.S. PATENT DOCUMENTS

| 3,809,811 | A | * | 5/1974 | Delisle et al. ................. 73/585 |
| 4,548,082 | A | * | 10/1985 | Engebretson et al. ......... 73/585 |
| 4,847,763 | A | * | 7/1989 | Moser et al. ............... 600/559 |
| 5,645,074 | A | * | 7/1997 | Shennib et al. ............. 600/559 |
| 5,732,396 | A | * | 3/1998 | Posen et al. ................. 704/267 |
| 6,602,202 | B1 | * | 8/2003 | John et al. ................... 600/559 |
| 2001/0040969 | A1 | * | 11/2001 | Revit et al. .................... 381/60 |

OTHER PUBLICATIONS

M.M. Taylor, *PEST: Efficient Estimates on Probability Function*, The Journal of the Acoustical Society of America, vol. 41, No. 4, pp. 782-787, Jan. 1967.
Audiologists' Desk Reference, vol. 1, pp. 82-84, 1997.
*Parrot Software*, pp. 1-36, 2000-2001.

* cited by examiner

*Primary Examiner*—David D. Knepper
(74) *Attorney, Agent, or Firm*—Elizabeth Arwine

(57) ABSTRACT

An improved method and system for performing speech intelligibility testing includes calibrating one or more recorded spoken words to have substantially the same sound energy and presenting the one or more calibrated recorded spoken words to a test subject. Speech intelligibility of the test subject is measured by utilizing the one or more calibrated recorded spoken words wherein the speech intelligibility measured is indicative of a percentage of the calibrated word or words that the test subject successfully identified.

16 Claims, 11 Drawing Sheets

DETERMINING SPEECH INTELLIGIBILITY

CROSS-REFERENCE TO RELATED APPLICATION

This patent application incorporates by reference in its entirety the subject matter of the currently co-pending U.S. patent application entitled, CALIBRATING AUDIOMETRY STIMULI, naming William A. Ahroon as inventor, filed substantially contemporaneously herewith.

This patent application incorporates by reference in its entirety the subject matter of the currently co-pending U.S. patent application entitled, DETERMINING SPEECH RECEPTION THRESHOLD, naming William A. Ahroon as inventor, filed substantially contemporaneously herewith.

STATEMENT REGARDING FEDERALLY SPONSORED RESEARCH OR DEVELOPMENT

This invention was made with government support awarded by the United States Army. The government has certain rights in this invention.

BACKGROUND OF THE INVENTION

1. Field of the Invention

The present application relates, in general, to audiometry. The present application relates, in particular, to speech audiometry.

2. Description of the Related Art

Audiometry is the testing of hearing acuity by use of an audiometer. An audiometer is an instrument for gauging and recording the acuity of human hearing.

There are various types of testing used in audiometry (e.g., pure-tone testing, or speech-based testing). In pure-tone testing, a person is usually fitted with headphones or positioned between speakers, and thereafter a series of single-tone (or frequency) sounds are played through the headphones or speakers. The person's responses to the played-back sounds are recorded (typically by a human tester, but sometimes by machine), and an assessment of the person's hearing acuity is made on the bases of the person's responses. In speech-based testing, like in pure-tone testing, a person is usually fitted with headphones or positioned between speakers. However, unlike pure-tone testing, in speech-based testing a series of spoken words are played back through the headphones or speakers. The person's responses to the played-back words are recorded (typically by a human tester), and an assessment of the person's hearing acuity is made on the bases of the person's responses.

One type of speech-based testing is speech intelligibility (SI) testing. SI testing generally provides a measure consisting of the percentage or proporation of words that are correctly reported from a series of spoken words. In typical SI testing, a person whose hearing is being tested is usually fitted with headphones or positioned between speakers, and thereafter the person is presented a series of words played through the headphones or speakers. The played back words are all intended to be at the same sound intensity, or loudness, which is generally ensured by making sure that the loudness control of the system through which the words are being played is the same for all played back words; that is, the loudness at which the system through which the words are being played back is controlled (e.g., the gain of amplifier driving the speakers or headphones through which the words are being played back). In response to each presented word, the person's whose hearing is under test indicates which word the person believes corresponds to the word which he or she has just heard through the speakers or microphones by repeating the word or selecting the word from a list supplied by the person conducting the test. In between the playback of each word, the individual conducting the SI testing records whether the test subject either correctly or incorrectly identified each such played back word. At the end of the test, the individual conducting the SI testing records the percentage correct, and such percentage thereafter serves as a measure of speech intelligibility.

BRIEF SUMMARY OF THE INVENTION

The inventor has devised a method and system which improve upon related-art SI Testing.

In one embodiment, a method includes but is not limited to presenting at least one calibrated spoken word; and measuring speech intelligibility utilizing the at least one calibrated spoken word.

In another embodiment, the presenting at least one calibrated spoken word is characterized by presenting the at least one calibrated spoken word having root-mean-squared calibration.

In another embodiment, the presenting at least one calibrated spoken word is characterized by presenting the at least one calibrated spoken word having peak value calibration.

In one or more various embodiments, related systems include but are not limited to circuitry and/or programming for effecting the foregoing-referenced method embodiments; the circuitry and/or programming can be virtually any combination of hardware, software, and/or firmware configured to effect the foregoing-referenced method embodiments depending upon the design choices of the system designer.

The foregoing is a summary and thus contains, by necessity; simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the non-limiting detailed description set forth herein.

BRIEF DESCRIPTION OF THE SEVERAL VIEWS OF THE DRAWING(S)

The use of the same symbols in different drawings typically indicates similar or identical items.

DETAILED DESCRIPTION OF THE INVENTION

Figure 1A:
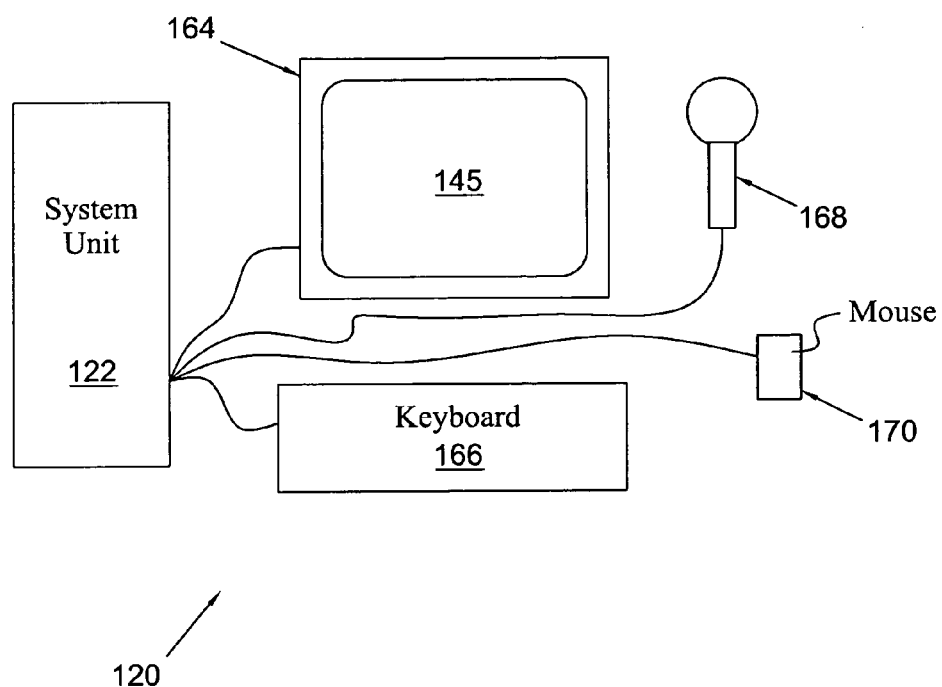
FIGS. 1A–1D, show, among other things, an environment wherein processes described herein may be implemented

As described in the "description of related art section", above, in related-art SI testing the played-back words are all intended to be at the same sound intensity, or loudness, and that a percentage measure of such equally-loud words serves as a measure of speech intelligibility.

The inventor has discovered the heretofore unrecognized fact that related-art SI testing has inaccuracies arising from lack of precision with respect to exactly what the person whose hearing is being tested is exposed to, and that this lack of precision impacts upon the efficacy of the related-art SI testing as well as the reproducibility of the related-art SI testing. Accordingly, the inventor has devised methods and systems which remedy the lack of precision of the related-art SI testing, and correspondingly give an increase in the efficacy and reproducibility of SI testing.

The inventor has noticed that, as regards words presented to an individual undergoing SI testing, while the loudness at which the system through which the words are being played back is controlled (e.g., the gain of amplifier driving the speakers or headphones through which the words are being played back), there is typically no (or very little) control over the energy (or intensity, or loudness) of the played-back words themselves. Consequently, the inventor has recognized that, insofar as SI testing is primarily based upon an assumption that the loudnesses of words played back to a person whose hearing is being tested is kept substantially constant, the fact that the played-back words themselves may have been recorded (or captured) with different energies (or intensities, or loudnesses) will introduce inaccuracies into the SI testing in that such differences in loudnesses can often somewhat offset the adjustment of the playback gain by the tester during testing. An extreme example of the foregoing would be where a first word (e.g., teak) was spoken and recorded in a normal tone of voice, and a second word (e.g., team) was spoken and recorded in a shouted tone of voice. Assuming the recording equipment itself were not altered between recording the two words, upon playback "team" would be perceived as appreciably louder than "teak," even if the gain of the playback system were kept constant across the two played-back words. The inventor has discovered that, in the case of SI testing, where assumed constant loudnesses between different words is primarily the basis for test assessment, such variations in the loudnesses or energies of the played-back words can become significant.

In light of the foregoing, the inventor has devised methods and systems whereby words used in SI testing are "calibrated" such that the words have substantially the same sound energy—at least as viewed against some common scale—which thus insures that the SI testing measures speech reception across words having the same or similar energies. As will be discussed following, two of the common scales which the inventor has used to calibrate the words are the Root Mean Squared (RMS) energies of a waveform representative of the words (e.g., a computer data file containing binary information representative of a voltage waveform produced by a microphone), and positive peak values (such positive peak values relative to a defined baseline) of waveforms representative of the words (e.g., a computer data file containing binary information representative of a voltage waveform produced by a microphone). However, it is to be understood that the methods and systems utilized herein are not limited to such scales. Rather, the methods and systems utilized herein may be extended to like systems where the words played back are calibrated against a common scale. For example, although positive peak values are described herein for ease of understanding, those having ordinary skill in the art will recognize that the schemes described herein can be extended to use peak to peak or peak magnitude scales via reasonable experimentation well within the ambit of one having ordinary skill in the art, and hence the present disclosure is not limited to the exemplary scales (e.g., RMS and positive peak) described herein.

Figure 1B:
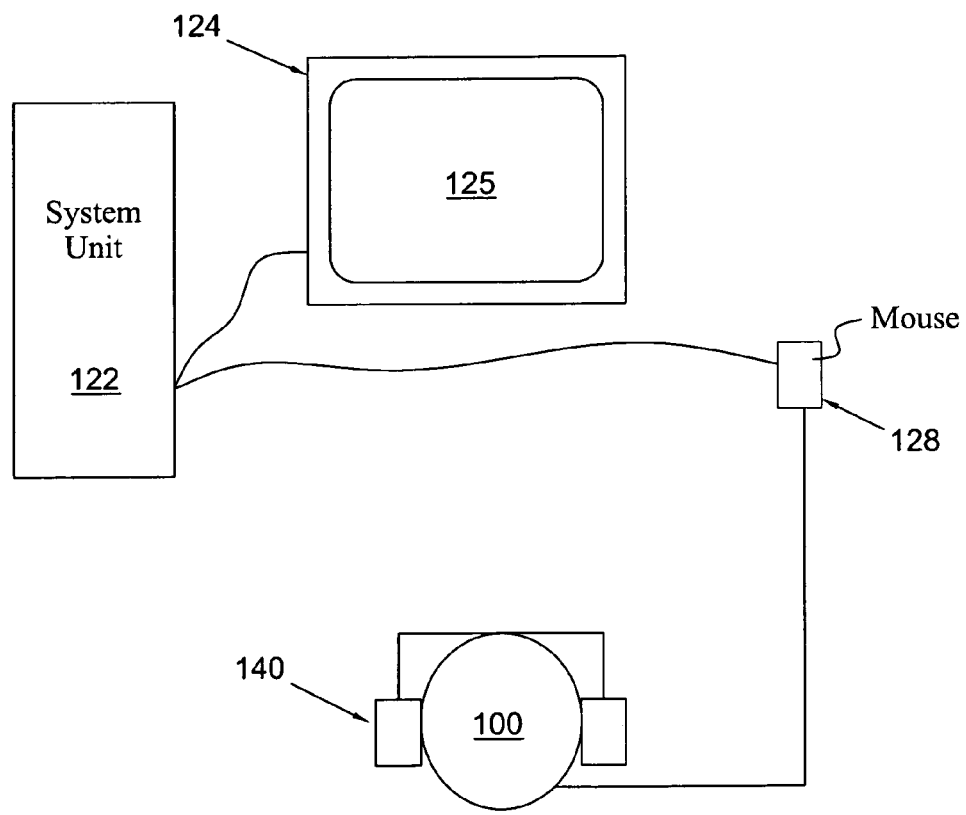

With reference to the figures, and in particular with reference now to FIGS. 1A–1D, shown, among other things, is an environment wherein processes described herein may be implemented. With reference now to FIG. 1A, shown is a view of data processing system 120 as it might appear if it were being accessed by a human operator (not shown) of a computer program running internal to system unit 122. Illustrated is graphical user interface (GUI) 145 appearing on video display device 164, with which the human operator may interact via some or all of keyboard 166, mouse 170, and microphone 168. Those skilled in the art will appreciate that in operation human test subject 100 (see FIG. 1B) and the human operator (not shown in FIG. 1A) would typically see and interact with different display devices (e.g., as shown in FIGS. 1A and 1B, respectively). Those skilled in the art willl also appreciate that system unit 122 of data processing system 120 may be configured, using equipment and techniques well-known to those having ordinary skill in the art, to drive the two different display devices 164, 124, and accept input from the two different mice 170, 128, respectively shown in FIGS. 1A and 1B. In FIG. 1A, GUI 145, video display device 164, mouse 170, and microphone 168 are all under the control of a computer program running internal to system unit 122. Those skilled in the art will recognize that system unit 122 typically houses one or more processors, communications, and memory devices.

Referring now to FIG. 1B, depicted is human test subject 100 interacting with GUI 125, appearing on video display device 124, via mouse 128 (which human test subject 100 is holding). Illustrated is that human test subject 100 is wearing headphones 140. GUI 125, video display device 124, mouse 128, and headphones 140 are all under the control of a computer program running internal to a system unit 122 (shown in FIG. 1A). GUI 125 depicts what in one implementation human test subject 100 sees when a computer program running internal to system unit 122 is executing a program which administers the Speech Intelligibility procedure as described herein. In one implementation of the Speech Intelligibility procedure human test subject 100 will indicate the word he believes he has heard through headphones 140 via using mouse 128 to "click" on the appropriate word of GUI 125, and the computer program will log his response as either correct or incorrect. At the end of the test, the computer program will calculate the percentage of answers correct as a measure of Speech Intelligibility.

Figure 1C:
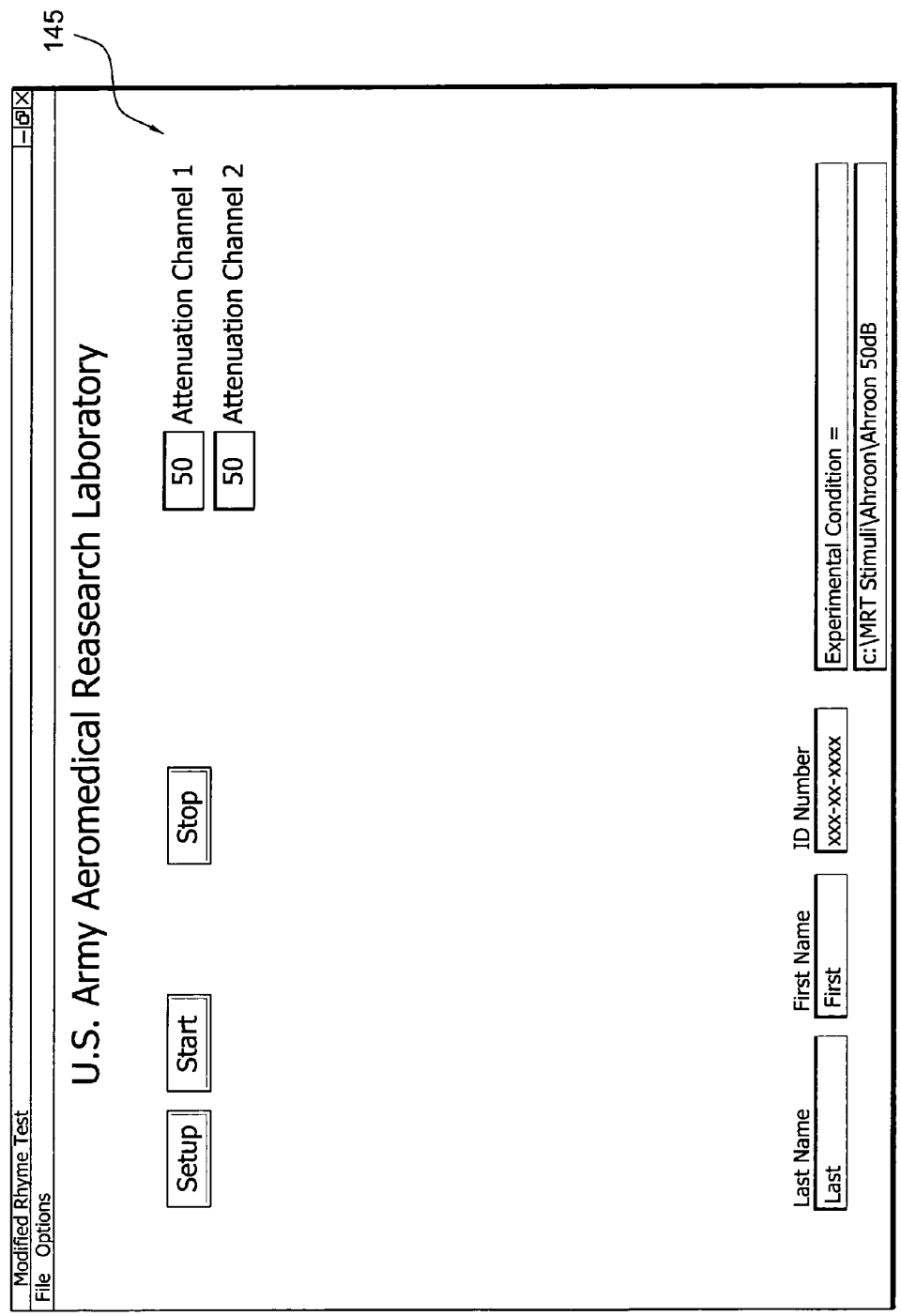

Referring now to FIG. 1C, shown is a close-up view of GUI 145 appearing in FIG. 1A. Depicted is that GUI 145 has adjustable GUI fields labeled "Attenuation (dB) Channel 1," and "Attenuation (dB) Channel 2," which can be adjusted by a test administrator. Human test subject 100 ordinarily will not see GUI 145.

Figure 1D:
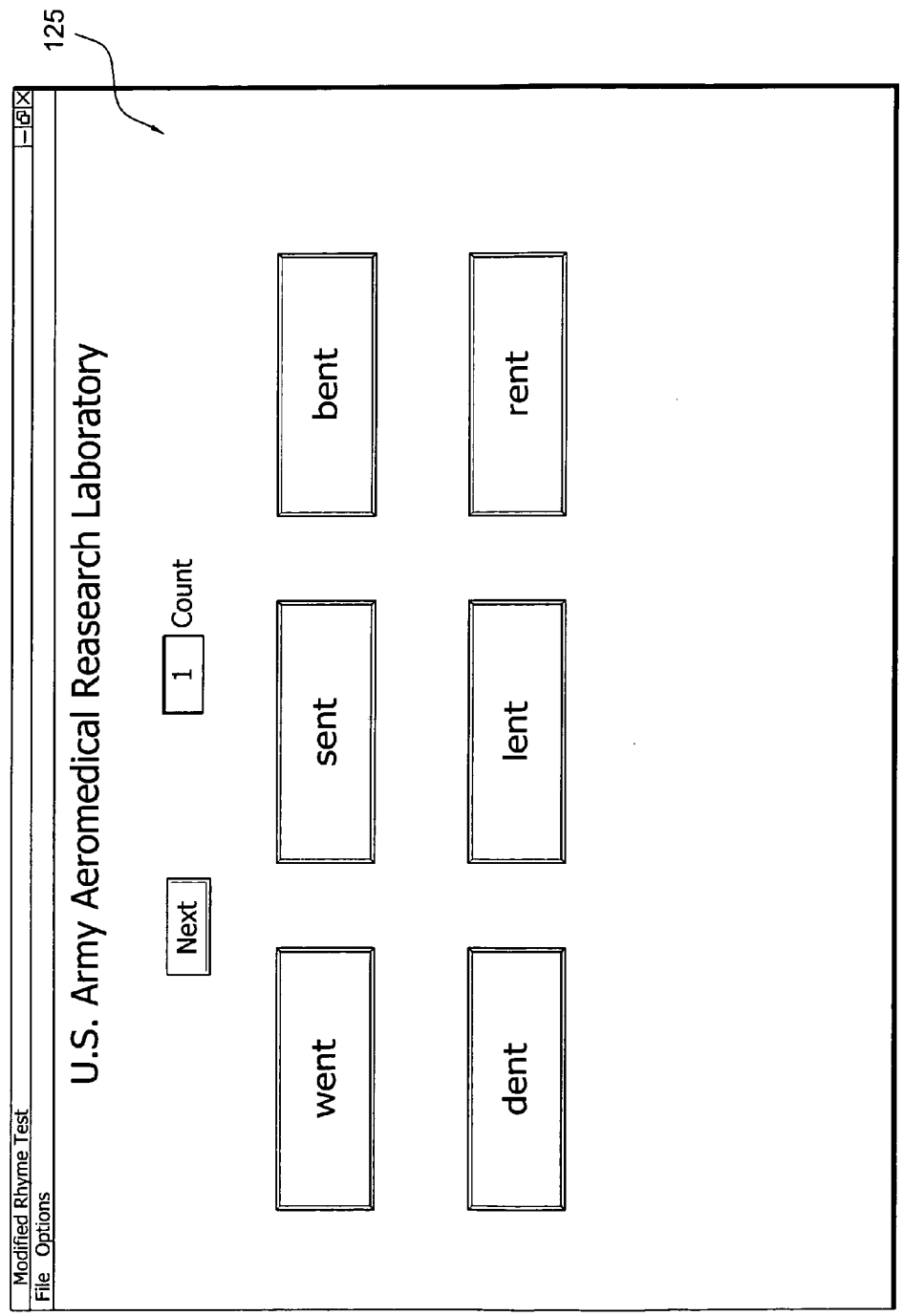

Referring now to FIG. 1D, shown is a close-up view of GUI 125, which as described above in relation to FIG. 1B shows a Speech Intelligibility procedure response screen. Depicted is that GUI 125 has a number of clickable controls, with each control labeled with a word (e.g., the icons labeled "went", "sent", "bent", etc.). In light of the disclosure herein (see below), those having ordinary skill in the art will recognize that GUI 125, as shown in FIG. 1D, is representative of a GUI which can be used with what is known in the art as the Modified Rhyme Test. Those skilled in the art will appreciate that, although the examples given here are particularly specified by the Modified Rhyme Test, the techniques set forth herein can easily be extended to another limited response set test via a minor amount of experimentation. For example, the teachings could relatively easily be modified to encompass the Diagnostic Rhyme Test, or a multiple-word Modified Rhyme Test (e.g., three words, each of the three words taken from a different six word ensemble with the subject having to identify all three presented words).

Following are a series of flowcharts depicting implementations of processes. For ease of understanding, the flowcharts are organized such that the initial flowcharts present implementations via an overall "big picture" viewpoint and thereafter the following flowcharts present alternate implementations and/or expansions of the "big picture" flowcharts as either substeps or additional steps building on one or more earlier-presented flowcharts. Those having ordinary skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations.

Figure 2:
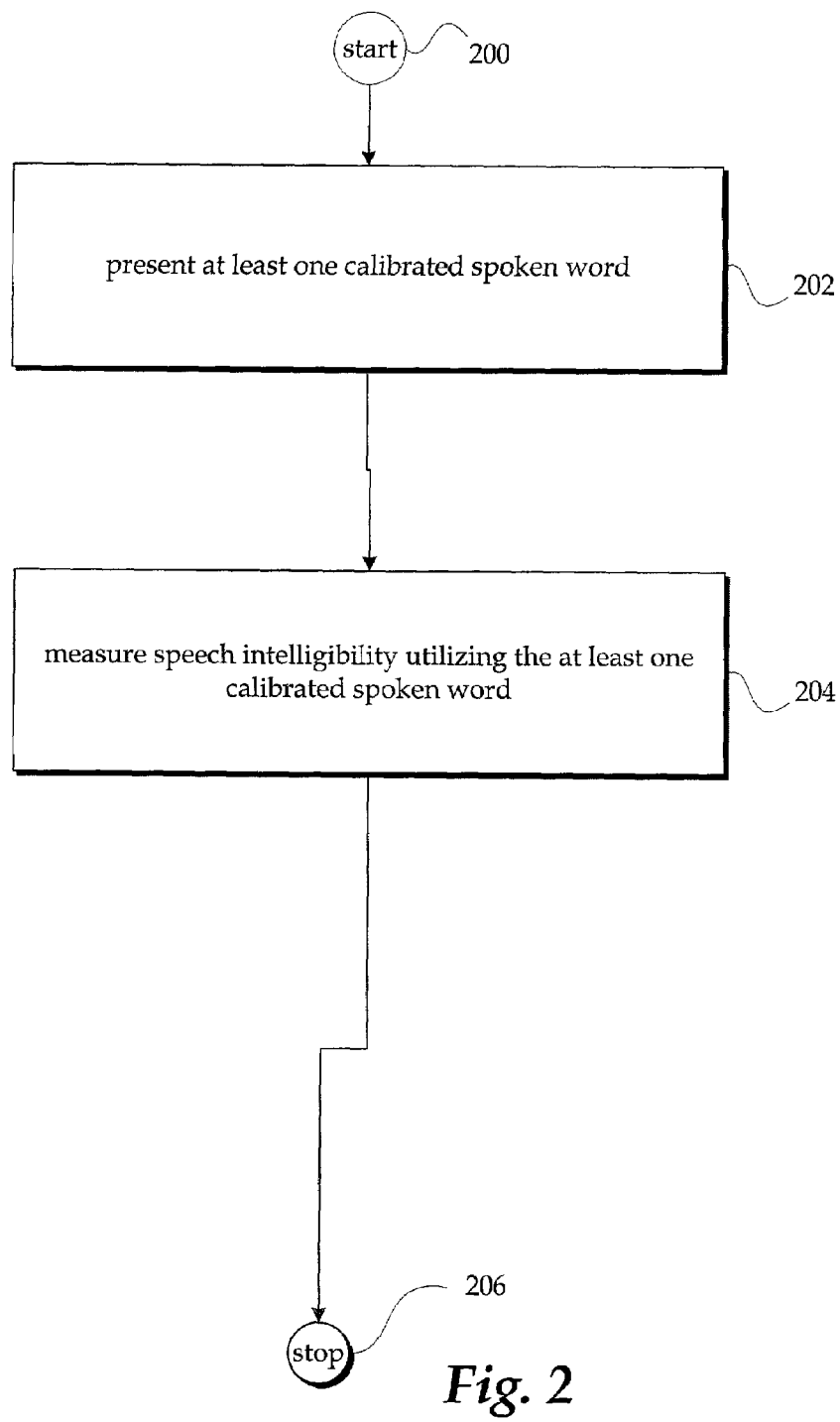
FIG. 2 shows a high-level logic flowchart depicting a process.

Referring now to FIG. 2, shown is a high-level logic flowchart depicting a process. Method step 200 illustrates the start of the process. Method step 202 depicts presenting at least one calibrated spoken word. Method step 204 illustrates measuring speech intelligibility utilizing the at least one calibrated spoken word. Method step 206 shows the end of the process. In one device implementation, method step 202 is achieved via a computer program, running internal to system unit 122, activating a Microsoft WAV file which is then played through headphones 140. In one device implementation, method step 204 is achieved via a computer program, running internal to system unit 122, calculating the speech intelligibility in response to a test subject selecting one or more words displayed via a GUI (e.g., the program calculating the speech intelligibility in response to human test subject 100 selecting a word from a displayed list of words, where the selection is via a clicking on one of the word-labeled GUI icons of GUI 125 via mouse 128).

Figure 3:
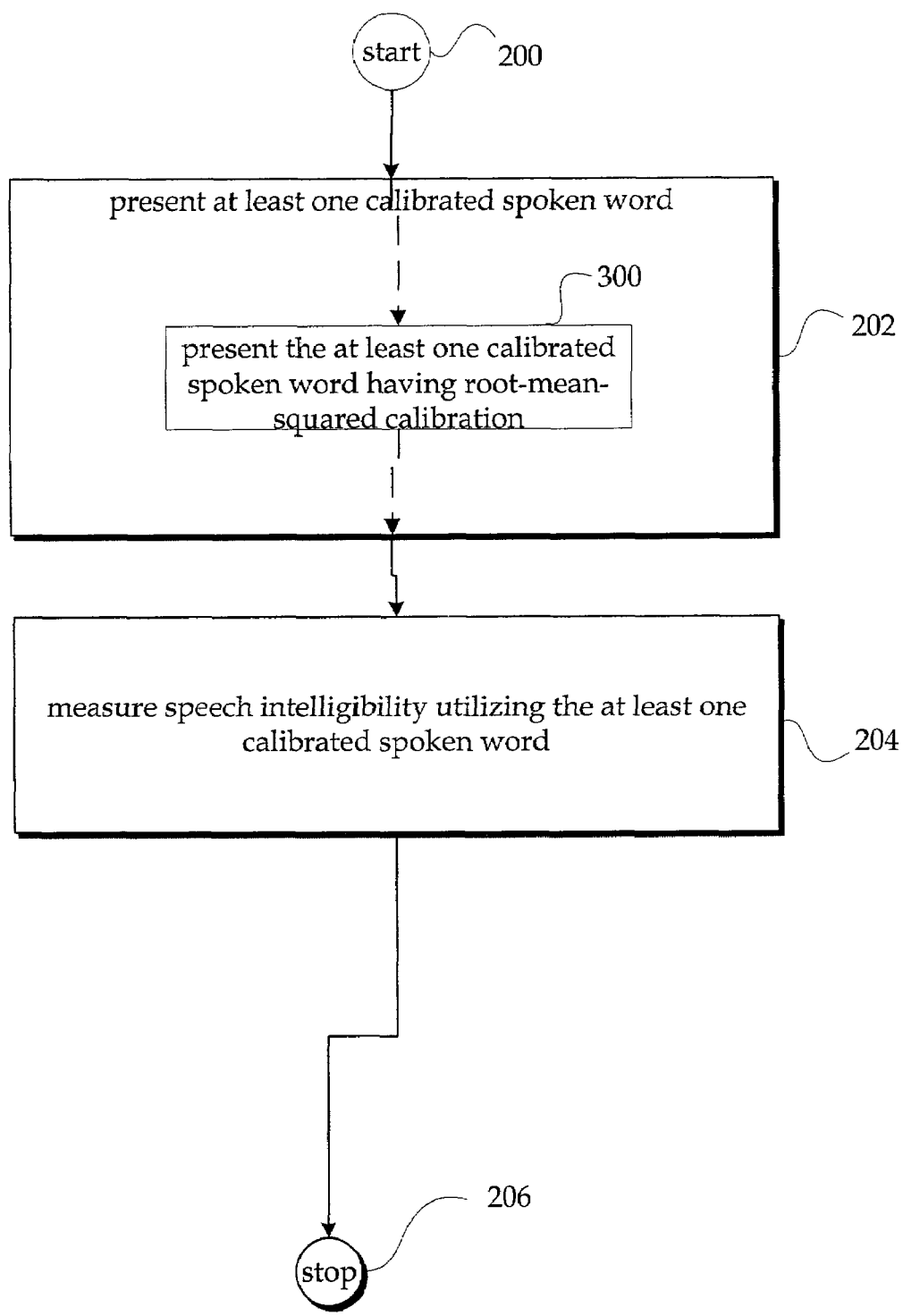
FIG. 3 shows an implementation of the high-level logic flowchart shown in FIG. 2.

With reference now to FIG. 3, shown is an implementation of the process depicted by the high-level logic flowchart shown in FIG. 2. Depicted in FIG. 3 is that in one implementation method step 202 can include method substep 300. Illustrated is that in one implementation presenting at least one calibrated spoken word can include, but is not limited to, presenting the at least one calibrated spoken word having root-mean-squared calibration. In one device implementation, method step 300 is achieved by a presentation of a succession of sound patterns of recorded words stored in a succession of Microsoft WAV files, where each recorded word has been scaled such that the RMS energy of the wave forms of the recorded words are substantially equal, and where each recorded word matches a word displayed on a GUI (e.g., presenting RMS-calibrated words corresponding to the word-labeled icons of GUI 125). The remaining method steps of FIG. 3 function substantially as described elsewhere herein.

Figure 4:
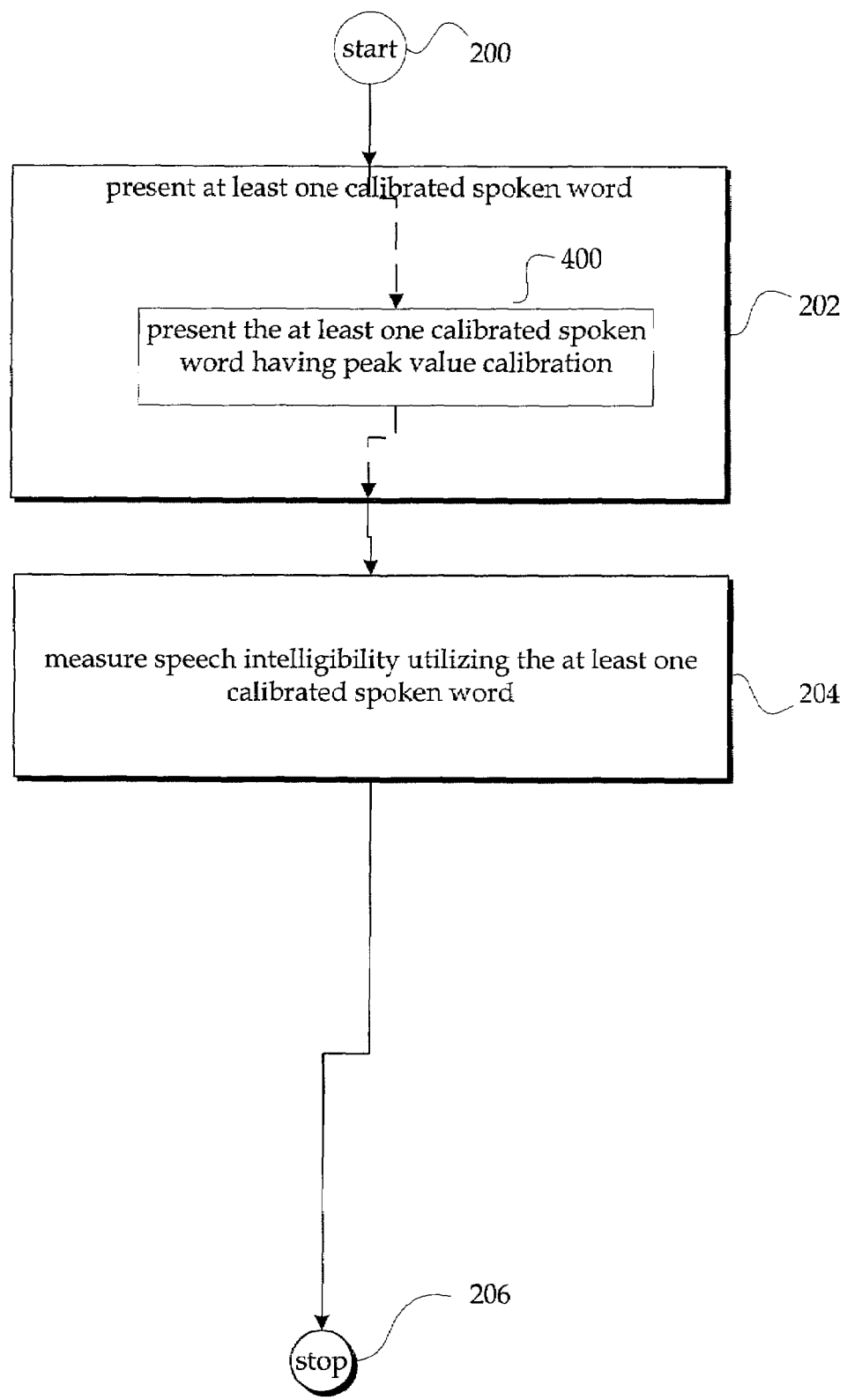
FIG. 4 shows an implementation of the high-level logic flowchart shown in FIG. 2.

With reference now to FIG. 4, shown is an implementation of the high-level logic flowchart shown in FIG. 2. Depicted in FIG. 4 is that in one implementation method step 202 can include method step 400. Illustrated is that in one implementation presenting at least one calibrated spoken word can include, but is not limited to, presenting the at least one calibrated spoken word having peak value calibration. In one device implementation, method step 400 is achieved by a computer program running internal to system unit 122 making a presentation of a succession of sound pattern waveforms representative of recorded words stored in Microsoft WAV files, where each recorded word has been scaled such that the positive peak value of the waveforms representative of the recorded words are substantially equal (those skilled in the art will appreciate that, as used herein, the positive peak criterion is to be representative of other peak-related criteria such as "peak-to-peak value," "maximum-absolute-peak value," etc. and that the modifications to utilize such other peak-related criteria would be well within the ambit of one having ordinary skill in the art in light of the teachings herein). The remaining method steps of FIG. 4 function substantially as described elsewhere herein.

Figure 5:
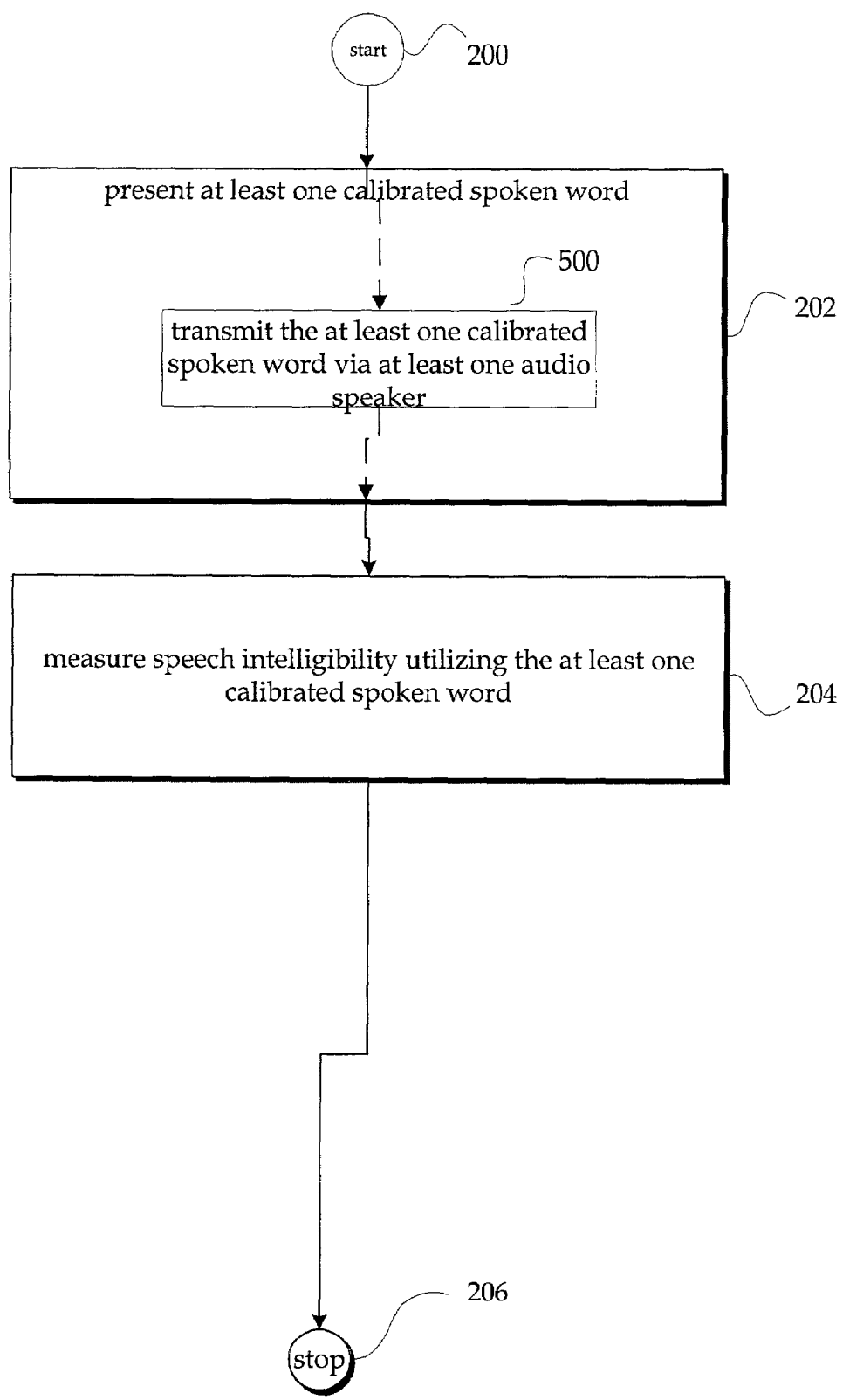
FIG. 5 shows an implementation of the high-level logic flowchart shown in FIG. 2.

With reference now to FIG. 5, shown is an implementation of the high-level logic flowchart shown in FIG. 2. Depicted in FIG. 5 is that in one implementation method step 202 can include method step 500. Illustrated is that in one implementation presenting at least one calibrated spoken word can include, but is not limited to, transmitting the at least one calibrated spoken word via at least one audio speaker. In one device implementation, method step 500 is achieved by a computer program running internal to system unit 122 playing a succession of calibrated spoken words through headphones 140. The remaining method steps of FIG. 5 function substantially as described elsewhere herein.

Figure 6:
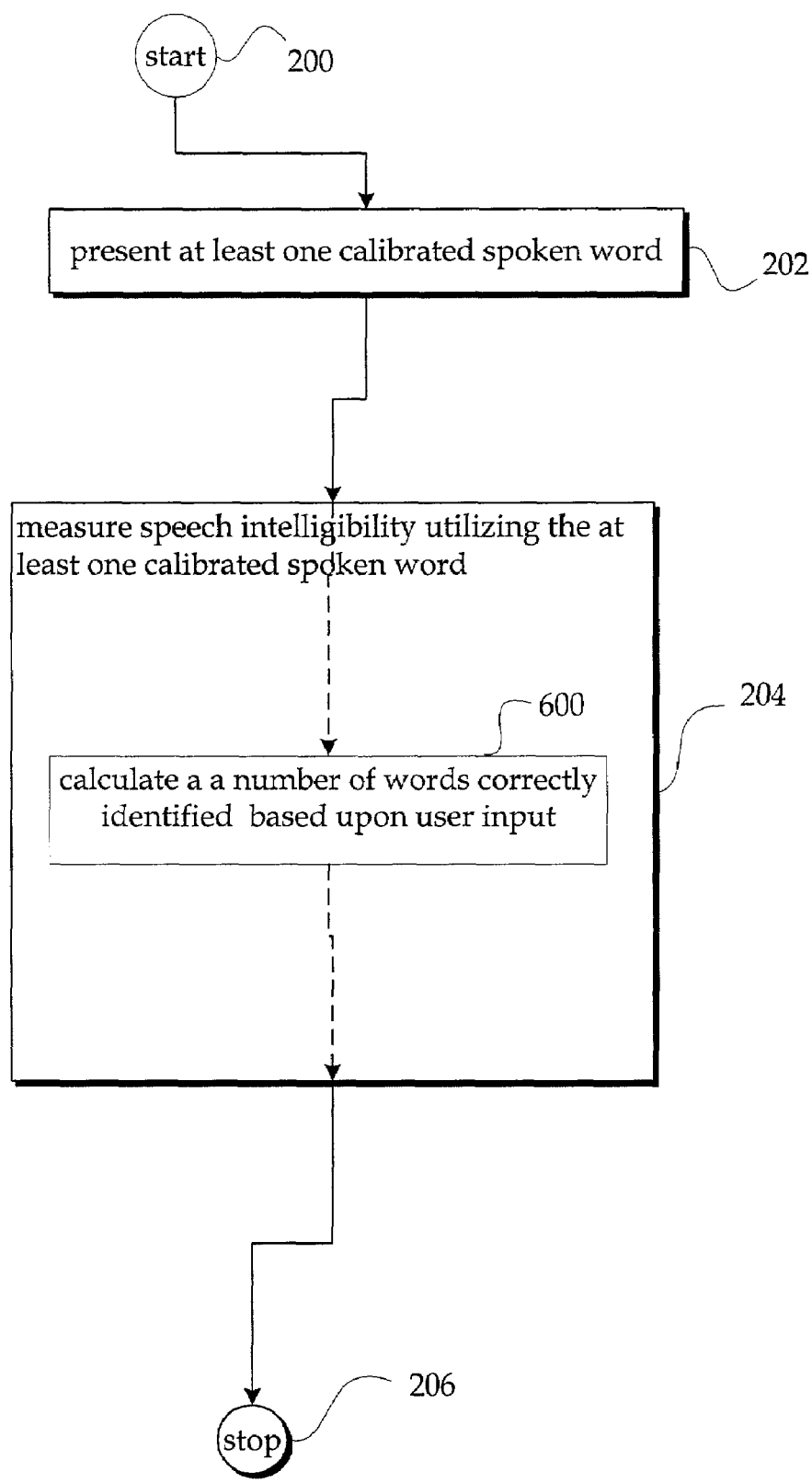
FIG. 6 shows an implementation of the high-level logic flowchart shown in FIG. 2.

With reference now to FIG. 6, shown is an implementation of the high-level logic flowchart shown in FIG. 2. Depicted in FIG. 6 is that in one implementation measuring speech intelligibility utilizing the at least one calibrated spoken word (method step 204) can include, but is not limited to, method step 600. Method step 600 illustrates calculating a number of words correctly identified based upon user input. In one device implementation, method step 600 is achieved via a computer program running internal to system unit 122 accepting test subject input via the test subject selecting a word from a list of words presented via a GUI (e.g., by pointing at and selecting ("clicking on") a control on GUI 125, displayed on video display device 124, via use of mouse 128).

The remaining method steps of FIG. 6 function substantially as described elsewhere herein.

Figure 7:
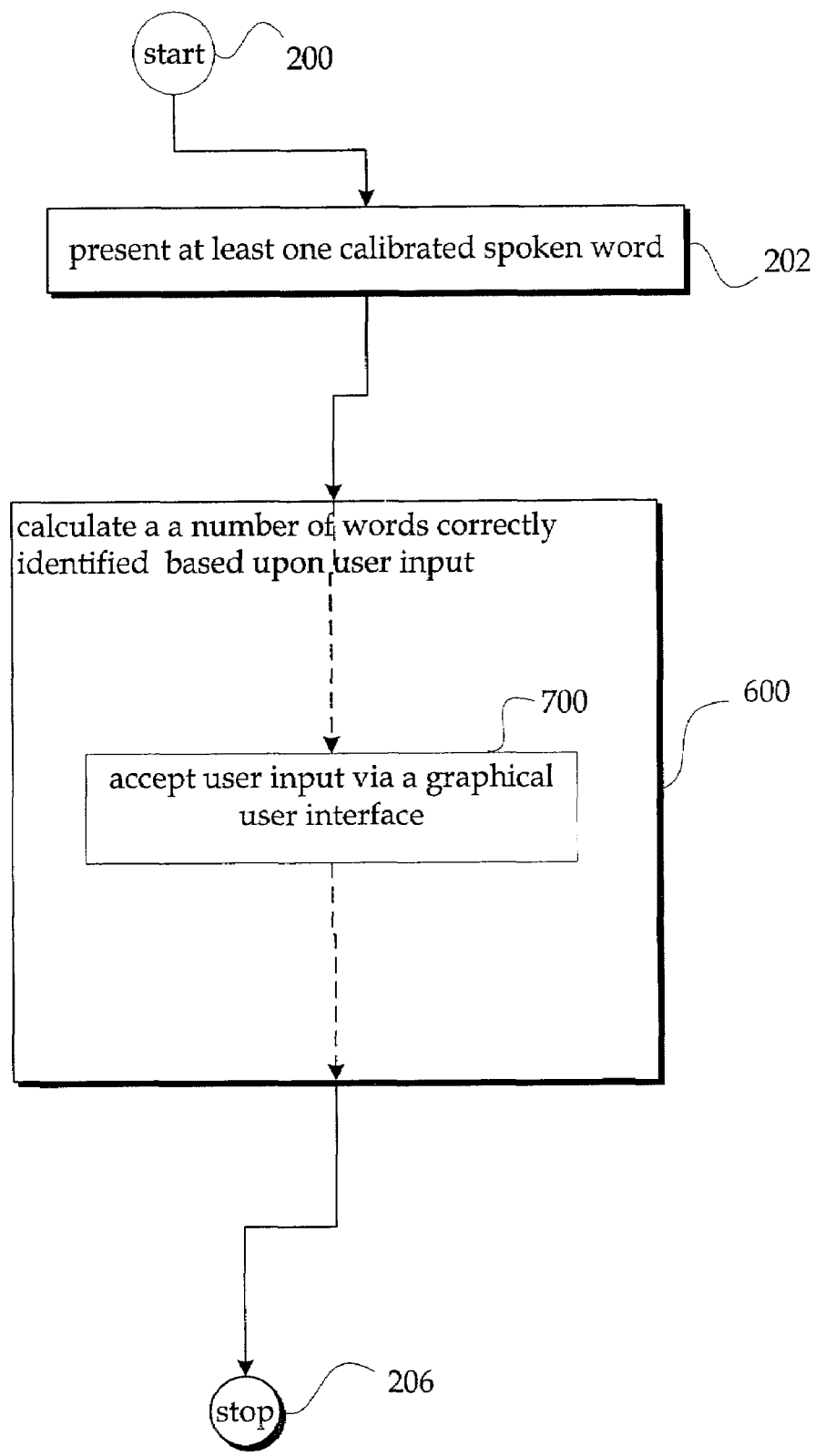
FIG. 7 shows an implementation of the high-level logic flowchart shown in FIG. 6.

With reference now to FIG. 7, shown is an implementation of the high-level logic flowchart shown in FIG. 6. Depicted in FIG. 7 is that in one implementation calculating a number of words correctly identified based upon user input (method step 600) can include, but is not limited to, method step 700. Method step 700 illustrates accepting user input via a graphical user interface. In one device implementation, method step 700 is achieved via acceptance of test subject input via the test subject selecting a word from a list of words presented via a GUI (e.g., by pointing at and clicking on a control on GUI 125 displayed on video display device 124 via use of mouse 128). The remaining method steps of FIG. 7 function substantially as described elsewhere herein.

Figure 8:
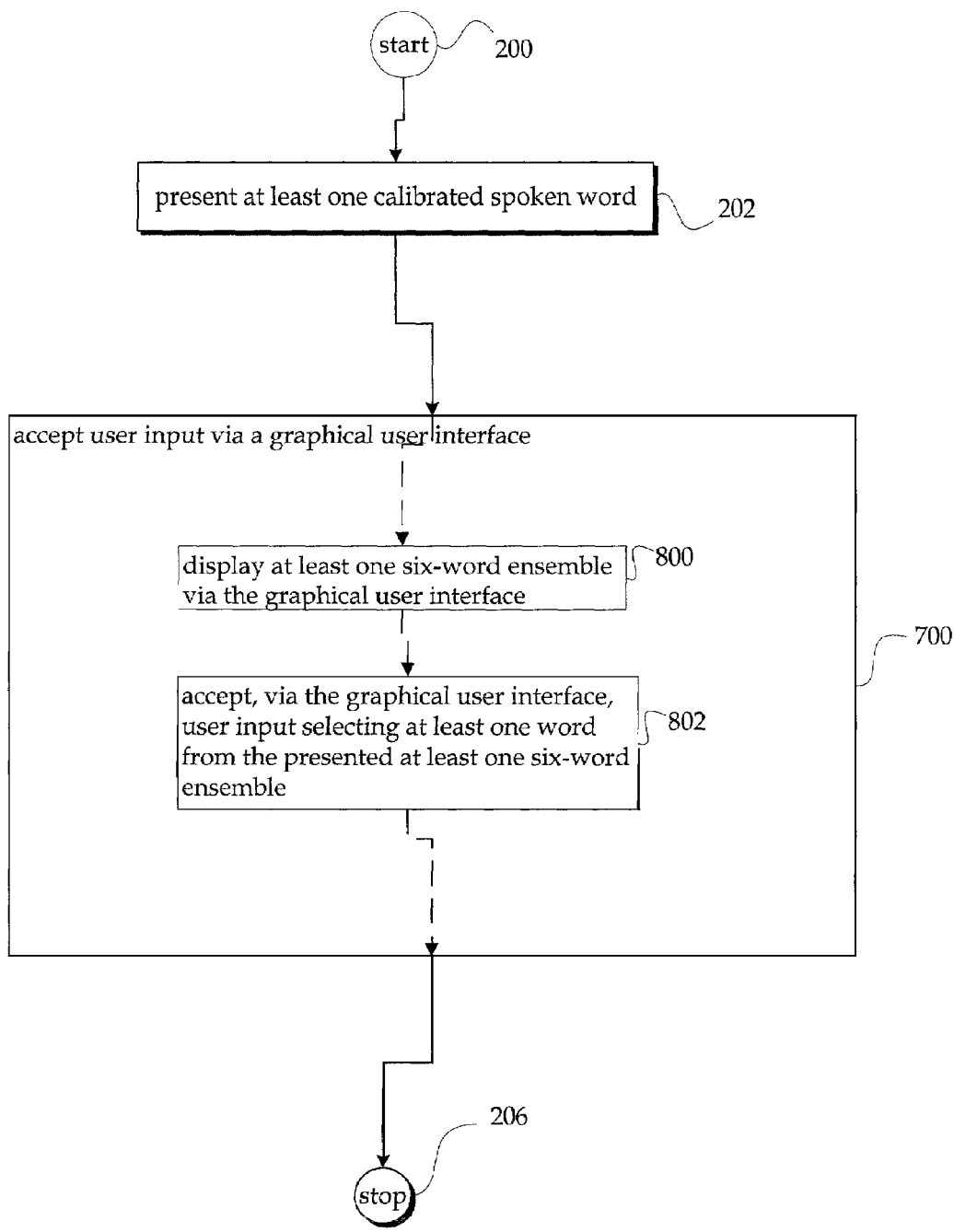
FIG. 8 shows an implementation of the high-level logic flowchart shown in FIG. 7.

With reference now to FIG. 8, shown is an implementation of the high-level logic flowchart shown in FIG. 7. Depicted in FIG. 8 is that in one implementation accepting user input via a graphical user interface (method step 700) can include, but is not limited to, method steps 800 and 802.

Method step 800 illustrates displaying at least one six-word ensemble via the graphical user interface. In one device implementation, method step 800 is achieved via a computer program running internal to system unit 122 presenting test subject 100 with a six-word ensemble via GUI 125. Method step 802 shows accepting, via the graphical user interface, user input selecting at least one word from the displayed at least one six word ensemble. In one device implementation, method step 800 is achieved via acceptance of test subject input via the test subject selecting a word from the six-word ensemble which has been presented via GUI 125 (e.g., by pointing at and clicking on a control of GUI 125 displayed on video display device 124 via use of mouse 128). The remaining method steps of FIG. 8 function substantially as described elsewhere herein.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will appreciate that there are various vehicles by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and examples. Insofar as such block diagrams, flowcharts, and examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. In one embodiment, the present invention may be implemented via Application Specific Integrated Circuits (ASICs). However, those skilled in the art will recognize that the embodiments disclosed herein, in whole or in part, can be equivalently implemented in standard Integrated Circuits, as one or more computer programs running on one or more computers (e.g., as one or more programs running on one or more computer systems), as one or more programs running on one or more processors (e.g., as one or more programs running on one or more micro-processors), as firmware, or as virtually any combination thereof, and that designing the circuitry and/or writing the code for the software and or firmware would be well within the skill of one of ordinary skill in the art in light of this disclosure. In addition, those skilled in the art will appreciate that the mechanisms of the present invention are capable of being distributed as a program product in a variety of forms, and that an illustrative embodiment of the present invention applies equally regardless of the particular type of signal bearing media used to actually carry out the distribution. Examples of signal-bearing media include, but are not limited to, the following: recordable type media such as floppy disks, hard disk drives, CD ROMs, digital tape, and computer memory; and transmission type media such as digital and analogue communication links using TDM or IP based communication links (e.g., packet links).

In a general sense, those skilled in the art will recognize that the various embodiments described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and electrical circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into data processing systems. That is, the devices and/or processes described herein can be integrated into a data processing system via a reasonable amount of experimentation. FIGS. 1A–1D shows an example representation of a data processing system into which at least a part of the herein described devices and/or processes may be integrated with a reasonable amount of experimentation.

With reference now again to FIGS. 1A–1D, depicted are a pictorial representations of a conventional data processing system in which portions of the illustrative embodiments of the devices and/or processes described herein may be implemented. It should be noted that graphical user interface systems (e.g., Microsoft Windows 98, Microsoft Windows NT, Microsoft Windows NT, Microsoft Windows 2000, or Microsoft Windows XP operating systems) and methods can be utilized with the data processing system depicted in FIGS. 1A–1D. Data processing system 120 is depicted which includes system unit 122, video display device 164, 124, keyboard 166, mice 170, 128, and microphone 168. Data processing system 120 may be implemented utilizing any suitable commercially available computer system.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method comprising:
    calibrating at least one recorded spoken word by controlling each of the at least one recorded spoken words to have substantially the same sound energy;
    presenting the at least one calibrated recorded spoken word to a test subject; and
    measuring speech intelligibility of the test subject by utilizing the at least one calibrated recorded spoken word, wherein the speech intelligibility measured is indicative of a percentage of the presented at least one calibrated spoken word or words that the test subject successfully identified.

2. The method of claim 1, wherein said presenting at least one calibrated spoken word comprises:
    presenting the at least one calibrated spoken word having root-mean-squared calibration.

3. The method of claim 1, wherein said presenting at least one calibrated spoken word comprises:
    presenting the at least one calibrated spoken word having peak value calibration.

4. The method of claim 1, wherein said presenting at least one calibrated spoken word comprises:
    transmitting the at least one calibrated spoken word via at least one audio speaker.

5. The method of claim 1, wherein said measuring speech intelligibility utilizing the at least one calibrated spoken word comprises:
    calculating a number of words correctly identified based upon user input.

6. The method of claim 5, wherein said calculating a number of words correctly identified based upon user input comprises:
    accepting user input via a graphical user interface.

7. The method of claim 6, wherein said accepting user input via a graphical user interface comprises:
    displaying at least one six word ensemble via the graphical user interface; and
    accepting, via the graphical user interface, user input selecting at least one word from the displayed at least one six word ensemble.

8. A system comprising:
    means for calibrating at least one recorded spoken word by controlling each of the at least one recorded spoken words to have substantially the same sound energy;
    means for presenting the at least one calibrated spoken word; and
    means for measuring speech intelligibility utilizing the at least one calibrated spoken word.

9. The system of claim 8, wherein said means for presenting at least one calibrated spoken word comprises:
    means for presenting the at least one calibrated spoken word having root-mean-squared calibration.

10. The system of claim 8, wherein said means for presenting at least one calibrated spoken word comprises:
    means for presenting at least one calibrated spoken word having peak value calibration.

11. The system of claim 8, wherein said means for presenting at least one calibrated spoken word comprises:
    means for transmitting the at least one calibrated spoken word via at least one audio speaker.

12. The system of claim 8, wherein said means for measuring speech intelligibility utilizing the at least one calibrated spoken word comprises:
    means for calculating a number of words correctly identified based upon user input.

13. The system of claim 12, wherein said means for calculating a number of words correctly identified based upon user input comprises:
    means for accepting user input via a graphical user interface.

14. The system of claim 13, wherein said means for accepting user input via a graphical user interface comprises:
    means for displaying at least one six word ensemble via the graphical user interface; and
    means for accepting, via the graphical user interface, user input selecting at least one word from the displayed at least one six word ensemble.

15. A program product comprising:
    means for calibrating at least one recorded spoken word by controlling each of the at least one recorded spoken words to have substantially the same sound energy;

means for presenting the at least one calibrated recorded spoken word to a test subject;

means for measuring a speech intelligibility of the test subject by utilizing the at least one calibrated recorded spoken word, wherein the speech intelligibility measured is indicative of a percentage of the presented at least one calibrated spoken word or words that the test subject successfully identified; and signal bearing media bearing said means for calibrating, means for presenting and means for measuring.

16. The program product of claim 15, wherein the signal bearing media comprise:

transmission media or recordable media.

* * * * *